(12) United States Patent
Schaefer et al.

(10) Patent No.: US 7,375,238 B2
(45) Date of Patent: May 20, 2008

(54) PROCESS FOR THE PREPARATION OF N-SUBSTITUTED 2-CYANOPYRROLIDINES

(75) Inventors: Frank Schaefer, Rheinfelden-Adelhausen (DE); Gottfried Sedelmeier, Schallstadt (DE)

(73) Assignee: Novartis AG, Basel (CH)

( * ) Notice: Subject to any disclaimer, the term of this patent is extended or adjusted under 35 U.S.C. 154(b) by 100 days.

(21) Appl. No.: 10/552,835

(22) PCT Filed: Apr. 15, 2004

(86) PCT No.: PCT/EP2004/003980

§ 371 (c)(1), (2), (4) Date: Oct. 13, 2005

(87) PCT Pub. No.: WO2004/092127

PCT Pub. Date: Oct. 28, 2004

(65) Prior Publication Data

US 2006/0199854 A1 Sep. 7, 2006

(30) Foreign Application Priority Data

Apr. 16, 2003 (GB) .................. 0308854.9
May 22, 2003 (GB) .................. 0311836.1

(51) Int. Cl.
*C07D 207/16* (2006.01)
(52) U.S. Cl. ..................................... 548/540
(58) Field of Classification Search .................. 548/540
See application file for complete search history.

(56) References Cited

U.S. PATENT DOCUMENTS 6,166,063 A * 12/2000 Villhauer ............ 514/423
6,380,398 B2   4/2002 Kanstrup et al. ........ 548/530

FOREIGN PATENT DOCUMENTS

WO   WO 98/19998    5/1998
WO   WO 00/34241    6/2000
WO   WO 01/96295 A2   12/2001
WO   WO 2004/092127   10/2004

OTHER PUBLICATIONS

Villhauer et al. J. Med. Chem. 2003, 46, 2774-89.*
Willand et al., Tetrahedon 58, pp. 5741-5746, Solid and solution phase syntheses of the 2-cyanopyrrolidide DPP-IV inhibitor NVP-DPP728 (2002).

* cited by examiner

Primary Examiner—Rebecca Anderson
Assistant Examiner—Jason M Nolan
(74) Attorney, Agent, or Firm—Cynthia Zhang

(57) ABSTRACT

The present invention relates to a process for the preparation of a N-(N'-substituted glycyl)-2-cyanopyrrolidine comprising at least (a) reacting, in the presence of dimethylformamide, a compound of formula (V)

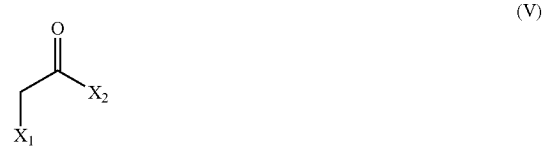

wherein, independently of each other, $X_1$ and $X_3$ are halogen; $X_2$ is halogen, OH, $O-C(=O)-CH_2X_3$, $-O-SO_2-(C_{1-8})$alkyl or 13 $O-SO_2$-(aryl), with L-prolinamide, followed by (b) reacting the resultant compound without isolation with a dehydration agent, optionally followed by (c) reacting, in the presence of a base, the resultant compound without isolation with an appropriate amine and (d) recovering the resultant compound in free form or in acid addition salt form.

7 Claims, No Drawings

PROCESS FOR THE PREPARATION OF N-SUBSTITUTED 2-CYANOPYRROLIDINES

The present invention relates to a novel process for the preparation of N-(N'-substituted glycyl)-2-cyanopyrrolidines and a composition obtainable according to the novel process comprising predominantly N-(N'-substituted glycyl)-2(S)-cyanopyrrolidine.

N-(N'-substituted glycyl)-2-cyanopyrrolidines, especially those of formula I

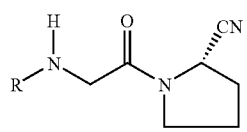

(I)

wherein R is as defined below; In free form or in acid addition salt form; are valuable dipeptidyl peptidase-IV (DPP-IV) inhibitors which have been described in WO 98/19998, for example.

The conventional process for preparation of N-(N'-substituted glycyl)-2-cyanopyrrolidines, especially those of formula I above, comprises reacting a halogen (preferably chlorine or bromine) substituted (2-cyanopyrrolidino)carbonylmethylene with an appropriate amine. Said substituted (2-cyanopyrrolidino)carbonylmethylene may be obtained by reacting a haloacetylhalide with L-prolinamide followed by a dehydration with trifluoroacetic anhydride. This process has significant drawbacks, especially when considering industrial production of N-(N'-substituted glycyl)-2-cyanopyrrolidines, as both the 1-haloacetyl-2-cyanopyrrolidine intermediate and its direct precursor are classified as irritant. Furthermore the process needs aqueous work up at several steps resulting in potential waste problems and lower yields. It has also recently been reported an alternative synthesis based on solid phase chemistry which avoids free 1-haloacetyl-2-cyanopyrrolidine but which process is not suitable for scale-up according to its authors (N. Willand et al., Tetrahedron 58 (2002) 5741-5746). Thus, there exists a need for an improved process.

It has now been found that surprisingly the 1-haloacetyl-2-cyanopyrrolidine intermediate may be prepared in such a way that no isolation of said irritant compound is needed. Said compound may therefore be directly further reacted with the appropriate amine. In addition, the new process allows to recycle all solvents and the only by-products are inorganic salts. The new process is characterised by a high overall yield and is suitable for industrial production.

Therefore, an object of the instant invention is the process for the preparation of a N-(N'-substituted glycyl)-2-cyanopyrrolidine comprising at least (a) reacting, in the presence of dimethylformamide, a compound of formula (V)

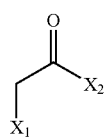

(V)

wherein, independently of each other, $X_1$ and $X_3$ are halogen; $X_2$ is halogen, OH, O—C(=O)—CH$_2$X$_3$, —O—SO$_2$—(C$_{1-8}$)alkyl or —O—SO$_2$-(aryl), with L-prolinamide, followed by (b) reacting the resultant compound without isolation with a dehydration agent, optionally followed by (c) reacting, in the presence of a base, the resultant compound without isolation with an appropriate amine and (d) recovering the resultant compound in free form or in acid addition salt form.

When $X_2$ is —O—SO$_2$-(aryl), the term "aryl" refers to monocyclic or bicyclic aromatic hydrocarbon groups having 6-12 carbon atoms in the ring portion, such as phenyl, biphenyl, naphthyl and tetrahydronaphthyl, each of which may optionally be substituted by 1-4 substituents, such as optionally substituted (C$_{1-4}$)alkyl e.g. trifluoromethyl, halo, hydroxy, (C$_{1-4}$)alkoxy, acyl. Preferably the aryl group is a phenyl, or a substituted phenyl.

When $X_2$ is —O—SO$_2$—(C$_{1-8}$)alkyl or —O—SO$_2$-(aryl), the term "alkyl" refers to either straight or branched chain, which may optionally be substituted by 1-5 substituents selected from halogen preferably fluorine, chlorine, bromine or iodine. Exemplary alkyl groups include methyl, ethyl, propyl, isopropyl, n-butyl, t-butyl, isobutyl, trifluoromethyl.

In the above described process, the amine is either a primary or a secondary amine. Such kind of amines useful in organic chemistry, for the synthesis of pharmaceutical compounds are well known by the person skilled in the art. An appropriate amine substituted by one or two organic groups, can be easily selected by the person skilled in the art based on e.g. the structure of the published DPP-IV inhibitors such as in WO 03/002596.

Specifically, an object of the instant invention is the process for the preparation of a compound of formula (I)

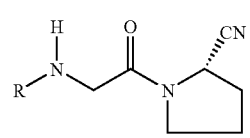

(I)

wherein R is
a) $R_1R_{1a}N(CH_2)_m$— wherein
   $R_1$ is a pyridinyl or pyrimidinyl moiety optionally mono- or independently disubstituted with (C$_{1-4}$)alkyl, (C$_{1-4}$)alkoxy, halogen, trifluoromethyl, cyano or nitro; or phenyl optionally mono- or independently disubstituted with (C$_{1-4}$)alkyl, (C$_{1-4}$)alkoxy or halogen;
   $R_{1a}$ is hydrogen or (C$_{1-8}$)alkyl; and
   m is 2 or 3;
b) (C$_{3-12}$)cycloalkyl optionally monosubstituted in the 1-position with (C$_{1-3}$)hydroxyalkyl;
c) $R_2(CH_2)_n$— wherein either
   $R_2$ is phenyl optionally mono- or independently di- or independently trisubstituted with (C$_{1-4}$)alkyl, (C$_{1-4}$)alkoxy, halogen or phenylthio optionally monosubstituted in the phenyl ring with hydroxymethyl; or is (C$_{1-8}$)alkyl; a [3.1.1]bicyclic carbocyclic moiety optionally mono- or plurisubstituted with (C$_{1-8}$)alkyl; a pyridinyl or naphthyl moiety optionally mono- or independently disubstituted with (C$_{1-4}$)alkyl, (C$_{1-4}$)alkoxy or halogen; cyclohexenyl; or optionally substituted adamantyl; and
   n is 1 to 3; or $R_2$ is phenoxy optionally mono- or independently disubstituted with $(C_{1-4})$alkyl, $(C_{1-4})$alkoxy or halogen; and n is 2 or 3;

d) $(R_3)_2CH(CH_2)_2$— wherein each $R_3$ independently is phenyl optionally mono- or independently-disubstituted with $(C_{1-4})$alkyl, $(C_{1-4})$alkoxy or halogen;

e) $R_4(CH_2)_p$— wherein $R_4$ is 2-oxopyrrolidinyl or $(C_{2-4})$alkoxy and p is 2 to 4;

f) isopropyl optionally monosubstituted in 1-position with $(C_{1-3})$hydroxyalkyl; or g) $R_5$ wherein $R_5$ is: indanyl; a pyrrolidinyl or piperidinyl moiety optionally substituted with benzyl; a [2.2.1]- or [3.1.1]bicyclic carbocyclic moiety optionally mono- or plurisubstituted with $(C_{1-8})$alkyl; adamantyl; substituted adamantly; or $(C_{1-8})$alkyl optionally mono- or independently plurisubstituted with hydroxy, hydroxymethyl or phenyl optionally mono-or independently disubstituted with $(C_{1-4})$alkyl, $(C_{1-4})$alkoxy or halogen;

in free form or in acid addition salt form comprising (a) reacting, in the presence of dimethylformamide, a compound of formula (V)

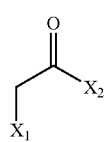

(V)

wherein, independently of each other, $X_1$ and $X_3$ are halogen; $X_2$ is halogen, OH, O—C(=O)—$CH_2X_3$, —O—$SO_2$—$(C_{1-8})$alkyl or —O—$SO_2$-(aryl), with L-prolinamide, followed by (b) reacting the resultant compound without isolation with a dehydration agent, preferably optionally followed by (c) reacting, in the presence of a base, the resultant compound without isolation with an appropriate amine, preferably a compound of formula (VI)

$H_2NR$ (VI)

wherein R is as defined for formula (I) and (d) recovering the resultant compound in free form or in acid addition salt form.

Reaction (a) is conveniently carried out under an inert atmosphere and in the presence of dimethylformamide and a further inert, organic solvent or a mixture of such solvents, preferably isopropyl acetate or ethyl acetate. The temperature preferably is from about 5° to about 45° C. and most preferred from about 10° to about 35° C. Preferably a 2 to 20% molar excess of (V) is used. Preferably, no base is added. Preferred are compounds of formula (V) wherein both $X_1$ and $X_2$ are halogen, preferably chlorine or bromine, particularly preferred $X_1$ and $X_2$ are the same and most preferred $X_1$ and $X_2$ are both chlorine.

Reaction (b) is conveniently carried out under an inert atmosphere and in the presence of an inert, organic solvent, preferably a mixture of isopropyl acetate and dimethylformamide. The temperature preferably is from about 15° to about 45° C. and most preferred from about 20° to about 35° C. Suitable dehydration agents are (haloalkylene)dialkylammonium halides, wherein the alkyl or alkylene is a, preferably straight, carbon chain of 1 to 4 carbon atoms, most preferred methyl or methylene, and halogen is chloro, bromo or iodo, most preferred chloro. Most preferred as a dehydration agent is the Vilsmeier reagent i.e. chloromethylene) dimethylammonium chloride. Preferably a 2 to 20% molar excess of the dehydration agent is used. Subsequently any excess of Vilsmeier reagent may be decomposed by the addition of a small amount of water.

Reaction (c) is conveniently carried out under an inert atmosphere whereby the resultant reaction product of (b) is added to a solution or suspension of the amine compound of formula (VI) in an inert, organic solvent, preferably 2-butanone, aceton, acetonitrile or dimethylformamide The temperature preferably is from about 5° to about 60° C. and most preferred from about 10° to about 35° C. Preferably a catalytic amount (for example 1 to 10%, preferably about 5%) of potassium iodide is used. The amine of formula (VI) is used in 5 to 35% molar excess, preferably in 10 to 25% molar excess. Conveniently the base, used in an amount of 2 to 10 eq, preferably about 5.5 eq, may be an alkali carbonate or NaOH, preferably $Na_2CO_3$ or $K_2CO_3$ and most preferred $K_2CO_3$.

Recovery (d) conveniently comprises filtering the reaction mixture, removing the solvents under reduced pressure and recrystallising the crude product from a solvent containing an organic or inorganic base. In a preferred embodiment, the solvent contains a N-base, for example 1,8-diazabicyclo[5.4.0]undec-7-ene, tetramethylguanidine, $N(C_4H_9)_3$, $N(C_2H_5)_3$, isobutylmorpholine or tetramethylpiperidine.

The compounds of formula (I) can exist in "free form" or in acid addition salt form. Salt forms may be recovered from the "free form" in known manner and vice versa. Acid addition salts may e.g. be those of pharmaceutically acceptable organic or inorganic acids. Although the preferred acid addition salts are the hydrochlorides, salts of methanesulfonic, sulfuric, phosphoric, citric, lactic and acetic acid may also be utilized.

"Alkyl" and "alkoxy" are either straight or branched chain, of which examples of the latter are isopropyl and tert-butyl.

R preferably is a) or c) as defined above.

$R_1$ preferably is a pyridinyl or pyrimidinyl or piperazinyl moiety optionally substituted as defined above. $R_{1a}$ preferably is hydrogen. $R_2$ preferably is optionally substituted phenyl or adamantyl. $R_3$ preferably is unsubstituted phenyl. $R_4$ preferably is alkoxy as defined above. $R_5$ preferably is optionally substituted alkyl as defined above, m preferably is 2. n preferably is 1 or 2, especially 2. p preferably is 2 or 3, especially 3.

Pyridinyl preferably is pyridin-2-yl; it preferably is unsubstituted or monosubstituted, preferably in 5-position. Pyrimidinyl preferably is pyrimidin-2-yl. It preferably is unsubstituted or monosubstituted, preferably in 4-position. Preferred as substitutents for pyridinyl and pyrimidinyl are halogen, cyano and nitro, especially cyano.

When it is substituted, phenyl preferably is monosubstituted; it preferably is substituted with halogen, preferably chlorine, or methoxy. It preferably is substituted in 2-, 4- and/or 5-position, especially in 4-position.

$(C_{3-12})$cycloalkyl preferably is cyclopentyl or cyclohexyl. When it is substituted, it preferably is substituted with hydroxymethyl. $(C_{2-4})$alkoxy preferably is of 1 or 2 carbon atoms, it especially is methoxy. $(C_{1-8})$alkoxy preferably is of 3 carbon atoms, it especially is isopropoxy. Halogen is fluorine, chlorine, bromine or iodine, preferably fluorine, chlorine or bromine, especially chlorine. $(C_{1-8})$alkyl preferably is of 1 to 6, preferably 1 to 4 or 3 to 5, especially of 2 or 3 carbon atoms, or methyl. ($C_{1-4}$) alkyl preferably is methyl or ethyl, especially methyl. ($C_{1-3}$)hydroxyalkyl preferably is hydroxymethyl.

A [3.1.1]bicyclic carbocyclic moiety optionally substituted as defined above preferably is bicyclo[3.1.1]hept-2-yl optionally disubstituted in 6-position with methyl, or bicyclo [3.1.1]hept-3-yl optionally trisubstituted with one methyl in 2-position and two methyl groups in 6-position. A [2.2.1] bicyclic carbocyclic moiety optionally substituted as defined above preferably is bicyclo[2.2.1]hept-2-yl.

Naphthyl preferably is 1-naphthyl. Cyclohexene preferably is cyclohex-1-en-l-yl. Adamantyl preferably is unsubstituted or substituted by one or more, for example 2 substituents 1- or 2-adamantyl. Preferred substituents are selected from alkyl, —$OR_{10}$ or —$NR_{11}R_{12}$; where $R_{10}$, $R_{11}$ and $R_{12}$ are independently hydrogen, alkyl, $C_{1-8}$alkanoyl, carbamyl, or —$CONR_{13}R_{14}$; where $R_{13}$ and $R_{14}$ are independently alkyl, unsubstituted or substituted aryl and where one of $R_{13}$ and $R_{14}$ additionally is hydrogen or $R_{13}$ and $R_{14}$ together represent $C_{2-7}$alkylene.

A pyrrolidinyl or piperidinyl moiety optionally substituted as defined above preferably is pyrrolidin-3-yl or piperidin-4-yl. When it is substituted it preferably is N-substituted.

Very preferred are compounds of formula (I)

wherein

R is $R_2(CH_2)_n$— and $R_2$ is substituted adamantyl; and n is 0, 1, 2 or 3; in free form or in acid addition salt form;

A preferred group is one of above compounds of formula (I) wherein the substituent on the adamantyl is bonded on a bridgehead.

Especially preferred compounds are compounds of formula

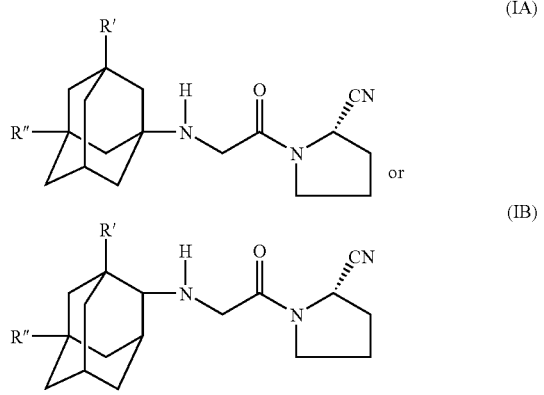

(IA)

or (IB)

wherein R' is hydroxy, $C_{1-7}$alkoxy, $C_{1-8}$alkanoyloxy, or R'''R''''N—C(O)O—, where R''' and R'''' independently are $C_{1-7}$alkyl or phenyl which is unsubstituted or substituted by a substituent selected from $C_{1-7}$alkyl, $C_{1-7}$alkoxy, halogen and trifluormethyl and where R''' additionally is hydrogen; or R''' and R'''' together are $C_{3-6}$alkylene; and R'' is hydrogen; or R' and R'' independently are $C_{1-7}$alkyl; in free form or in acid addition salt form.

Very particularly preferred is the compound of formula (IA) wherein R' is hydroxy and R'' is hydrogen in free form or in acid addition salt form. This compound is also known as pyrrolidine, 1-[(3-hydroxy-1-adamantyl)amino]acetyl-2-cyano-, (S) or LAF237.

The preferred appropriate amine, is a compound of formula (VI)

$$H_2NR \quad (VI)$$

wherein the preferred R are the same as those defined for formula (I), especially R is $R_2(CH_2)_n$— and $R_2$ is substituted adamantly especially as defined above; and n is 0, 1, 2 or 3; in free form or in acid addition salt form;

The compounds of formula (I) exist in the form of optically active isomers or stereoisomers and can be separated and recovered by conventional techniques, however the above described process is capable of yielding compounds of formula (I) with a high (at least 95%) enantiomeric purity of the N-(N'-substituted glycyl)-2(S)-cyanopyrrolidine.

Therefore, a further object of the instant invention is a composition of N-(N'-substituted glycyl)-2(S)-cyanopyrrolidine and N-(N'-substituted glycyl)-2(R)-cyanopyrrolidine, obtainable according to the above described process, whereby 95% to 99.9% is N-(N'-substituted glycyl)-2(S)-cyanopyrrolidine and 5% to 0.1% is N-(N'-substituted glycyl)-2(R)-cyanopyrrolidine, especially whereby 98% to 99.9% is N-(N'-substituted glycyl)-2(S)-cyanopyrrolidine and 2% to 0.1% is N-(N'-substituted glycyl)-2(R)-cyanopyrrolidine and preferably whereby 98% to 99.99% is N-(N'-substituted glycyl)-2(S)-cyanopyrrolidine and 2% to 0.01% is N-(N'-substituted glycyl)-2(R)-cyanopyrrolidine, and very preferably whereby 99% to 99.99% is N-(N'-substituted glycyl)-2(S)-cyanopyrrolidine and 1% to 0.01% is N-(N'-substituted glycyl)-2(R)-cyanopyrrolidine.

In a further embodiment the present invention covers a composition e.g. a pharmaceutical composition comprising a N-(N'-substituted glycyl)-2(S)-cyanopyrrolidine and a N-(N'-substituted glycyl)-2(R)-cyanopyrrolidine, whereby 95% to 99.9% is N-(N'-substituted glycyl)-2(S)-cyanopyrrolidine and 5% to 0.1% is N-(N'-substituted glycyl)-2(R)-cyanopyrrolidine, preferably whereby 95% to 99.99% is N-(N'-substituted glycyl)-2(S)-cyanopyrrolidine and 5% to 0.01% is N-(N'-substituted glycyl)-2(R)-cyanopyrrolidine, most preferably whereby 98% to 99.99% is N-(N'-substituted glycyl)-2(S)-cyanopyrrolidine and 2% to 0.01% is N-(N'-substituted glycyl)-2(R)-cyanopyrrolidine and very preferably whereby 99% to 99.99% is N-(N'-substituted glycyl)-2(S)-cyanopyrrolidine and 1% to 0.01% is N-(N'-substituted glycyl)-2(R)-cyanopyrrolidine. A preferred example is a composition e.g. a pharmaceutical composition of N-(N'-substituted glycyl)-2(S)-cyanopyrrolidine and N-(N'-substituted glycyl)-2(R)-cyanopyrrolidine, whereby 99% to 99.5% is N-(N'-substituted glycyl)-2(S)-cyanopyrrolidine and 1% to 0.5% is N-(N'-substituted glycyl)-2(R)-cyanopyrrolidine, or whereby 99.2% to 99.9% is N-(N'-substituted glycyl)-2(S)-cyanopyrrolidine and 0.8% to 0.1% is N-(N'-substituted glycyl)-2(R)-cyanopyrrolidine A further object of the instant invention is a composition of N-(N'-substituted glycyl)-2(S)-cyanopyrrolidine and/or N-(N'-substituted glycyl)-2(R)-cyanopyrrolidine, obtainable according to the above described process.

Preferably, the instant invention is a composition comprising N-(N'-substituted glycyl)-2(S)-cyanopyrrolidine and/or N-(N'-substituted glycyl)-2(R)-cyanopyrrolidine, wherein the only by-products are inorganic salts, preferably obtainable according to the above described process.

The present invention also concerns;

i) a pharmaceutical composition comprising, a) one or more pharmaceutically acceptable excipients, and b) at least one N-(N'-substituted glycyl)-2(S)-cyanopyrrolidine obtainable according to the above described process.

ii) a pharmaceutical composition comprising,
 a) one or more pharmaceutically acceptable excipients, and
 b) at least one N-(N'-substituted glycyl)-2(S)-cyanopyrrolidine, and
 c) between 0.00001% and 5% by weight of at least one (haloalkylene)dialkylammonium halide preferably chloromethylene)dimethylammonium chloride.

Preferably the N-(N'-substituted glycyl)-2(S)-cyanopyrrolidine is obtainable according to the above described process Preferred N-(N'-substituted glycyl)-2(S)-cyanopyrrolidines are those described as preferred compounds in the above process.

EXAMPLES

Example 1

Preparation of Pyrrolidine, 1-[(3-hydroxy-1-adamantyl)amino]acetyl-2-cyano-, (S)

Step (a)

A 1500 ml reactor, equipped with a mechanical stirrer, is charged with 212 g isopropyl-acetate and 19.8 g dimethylformamide. The reactor is inertized. At about IT (internal temperature) 15° C., 125 g chloroacetylchloride is added within 15 min., after complete addition the IT is adjusted to about 15° C., and a solution of 110 g L-prolinamide in 304 g dimethylformamide is added within 1 h. The addition funnel is rinsed with 18 g isopropyl-acetate. The reaction mixture is warmed to about IT 35° C. for 1.5 h.

Step (b)

After cooling to about 15° C. 142 g Vilsmeier reagent is added in portions. The reaction mixture is stirred for 1 h at about IT 25° C. At IT max. 25° C. 4.4 g water is added.

Step (c)

A 4.5 l reactor, equipped with a mechanical stirrer, is charged with 733 g of potassium carbonate, 194 g 3-hydroxyaminoadamantane, 8.0 g potassium iodide and 880 g 2-butanone. The suspension is heated to about 35° C. At this temperature 937 g solution of step b) (crude (S)-1-chloroacetyl-pyrrolidine-2-carbonitrile) is added within 1.5 h. The addition funnel is rinsed with 20 g 2-butanone. After stirring for an additional 1 h, the suspension is warmed to about IT 70° C. for 30 min. The warm suspension is filtered and the filter cake is rinsed three times with warm 331 g 2-butanone. The filtrate is concentrated at about JT (jacket temperature) 60° C. under reduced pressure (about 20 mbar).

Step (d)

At about JT 60° C. 8.8 g 1,8-diazabicyclo[5.4.0]undec-7-ene and 44 g isopropanol is added and stirred for 30 min. at IT about 60° C. The resulting suspension is cooled to about IT 40° C. and at JT 40° C. 814 g t-butylmethylether is added. The suspension is cooled to about IT 20° C. and stirred for at least 2 h at this temperature, then cooled to about −10° C.-0° C., stirred for 1 h and filtered. The filtration "cake" is washed twice with 168 g of a cold (about −10° C.) 1:1 (v:v) mixture of isopropanol and t-butylmethylether. The crude product (247 g) is dried under reduced pressure at about JT 55° C.

Example 2

Purification of Pyrrolidine, 1-[(3-hydroxy-1-adamantyl)amino]acetyl-2-cyano-, (S)

A 750 ml reactor, equipped with a mechanical stirrer, is charged with 199 g of crude 1-[(3-hydroxy-adamant-1-ylamino)-acetyl]-pyrrolidine-2(S)-carbonitrile), 800 g 2-butanone. The mixture is heated to reflux (JT 95° C.) and stirred for 15 min. The mixture is filtered into a warm (JT 75° C.) reactor, the filter cake is washed with 80 g 2-butanone. The IT is adjusted to 70° C. and 0.18 g (1-[(3-hydroxy-adamant-1-ylamino)-acetyl]-pyrrolidine-2(S)-carbonitrile) suspended in 1.6 g 2-butanone are added. The resulting suspension is stirred for 30 min., cooled to IT 50° C. within 2 h then to 30° C. within 1 h finally to 0° C. within 1 h and stirred for 1 additional h. After this the suspension is filtered and the crude product is washed twice with a cold (0° C.) mixture of 60.4 g 2-butanone and 55.5 g t-butyl methyl ether. The product is dried under reduced pressure at about JT 55° C. The melting point is 148° C.

What is claimed is:

1. A process for the preparation of a N-(N'-substituted glycyl)-2-cyanopyrrolidine comprising at least
 (a) reacting, in the presence of dimethylformamide, a compound of formula (V)

(V)

wherein, independently of each other, X1 and X3 are halogen; X2 is halogen, OH, O—C(=O)—CH$_2$X$_3$, —O—SO$_2$—(C$_{1-8}$)alkyl or —O—SO$_2$-(aryl), with L-prolinamide, followed by
 (b) reacting the resultant compound without isolation with a dehydration agent selected from (haloalkylene)dialkylammonium halide followed by
 (c) reacting, in the presence of a base, the resultant compound without isolation with an appropriate amine and
 (d) recovering the resultant compound in free form or in acid addition salt form.

2. A process according to claim 1 wherein the N-(N'-substituted glycyl)-2-cyanopyrrolidine is a compound of formula (I)

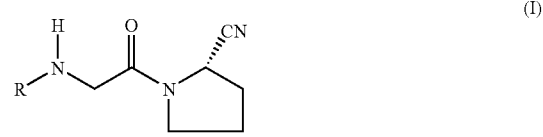

(I)

wherein R is
 a) R$_1$R$_{1a}$N(CH$_2$)$_m$— wherein
 R1 is a pyridinyl or pyrimidinyl moiety optionally mono- or independently disubstituted with (C$_{1-4}$)alkyl, (C$_{1-4}$) alkoxy, halogen, trifluoromethyl, cyano or nitro; or phenyl optionally mono- or independently disubstituted with (C$_{1-4}$)alkyl, (C$_{1-4}$)alkoxy or halogen;
 R1a is hydrogen or (C$_{1-8}$)alkyl; and m is 2 or 3;

b) $(C_{3-12})$cycloalkyl optionally monosubstituted in the 1-position with $(C_{1-3})$hydroxyalkyl;

c) $R_2(CH2)n$— wherein either $R_2$ is phenyl optionally mono- or independently di- or independently trisubstituted with $(C_{1-4})$alkyl, $(C_{1-4})$alkoxy, halogen or phenylthio optionally monosubstituted in the phenyl ring with hydroxymethyl; or is $(C_{1-8})$alkyl; a [3.1.1]bicyclic carbocyclic moiety optionally mono- or plurisubstituted with $(C_{1-8})$alkyl; a pyridinyl or naphthyl moiety optionally mono- or independently disubstituted with $(C_{1-4})$alkyl, $(C_{1-4})$alkoxy or halogen; cyclohexenyl; or optionally substituted adamantyl; and n is 1 to 3; or R2 is phenoxy optionally mono- or independently disubstituted with $(C_{1-4})$alkyl, $(C_{1-4})$alkoxy or halogen; and n is 2 or 3;

d) $(R_3)_2CH(CH_2)_2$— wherein each R3 independently is phenyl optionally mono- or independently disubstituted with $(C_{1-4})$alkyl, $(C_{1-4})$alkoxy or halogen;

e) $R_4(CH_2)_p$— wherein $R_4$ is 2-oxopyrrolidinyl or $(C_{2-4})$alkoxy and p is 2 to 4;

f) isopropyl optionally monosubstituted in 1-position with $(C_{1-3})$hydroxyalkyl; or g) $R_5$ wherein $R_5$ is: indanyl; a pyrrolidinyl or piperidinyl moiety optionally substituted with benzyl; a [2.2.1]- or [3.1.1]bicyclic carbocyclic moiety optionally mono- or multisubstituted with $(C_{1-8})$alkyl; adamantyl; substituted adamantyl; or $(C_{1-8})$alkyl optionally mono- or independently plurisubstituted with hydroxy, hydroxymethyl or phenyl optionally mono-or independently disubstituted with $(C_{1-4})$alkyl, $(C_{1-4})$alkoxy or halogen;

in free form or in acid addition salt form.

3. A process according to claim 1 wherein the dehydration agent of step (b) is (chloromethylene)dimethylammonium chloride.

4. A process according to claim 2 wherein the amine of step (c) is a compound of formula (VI)

$$H_2NR \qquad (VI)$$

wherein R is as defined for formula (I) in claim 2.

5. A process according to claim 2 comprising (a) reacting, in the presence of dimethylformamide, a compound of formula (V)

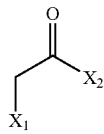

(V)

wherein $X_1$ is halogen; $X_2$ is halogen, OH, O—C(=O)—CH$_2$X, —O—SO$_2$—(C1-8)alkyl or —O—SO$_2$-(aryl), with L-prolinamide, followed by (b) reacting the resultant compound without isolation with (chloromethylene)dimethylammonium chloride, followed by (c) reacting, in the presence of a base, the resultant compound without isolation with a compound of formula (VI)

$$H_2NR \qquad (VI)$$

wherein R is as defined for formula (I) and (d) recovering the resultant compound in free form or in acid addition salt form.

6. A process according to claim 5 wherein R is $R_2(CH_2)_n$— and $R_2$ is substituted adamantyl; and n is 0, 1, 2 or 3.

7. A process according to claim 2 herein the dehydration agent of step (b) is (chloromethylene)dimethylammonium chloride.

* * * * *